United States Patent [19]

Le Pecq et al.

[11] Patent Number: 4,483,989

[45] Date of Patent: Nov. 20, 1984

[54] SYNTHESIS OF PYRIDO[4,3-B]CARBAZOLE DERIVATIVES

[75] Inventors: Jean-Bernard Le Pecq; Claude Paoletti, both of Paris; Nguyen Dat-Xuong, Antony, all of France

[73] Assignee: Agence Nationale de Valorisation de la Recherche (ANVAR), Neuilly-sur-Seine, France

[21] Appl. No.: 307,296

[22] Filed: Sep. 30, 1981

Related U.S. Application Data

[60] Division of Ser. No. 942,793, Sep. 15, 1978, Pat. No. 4,310,667, which is a continuation-in-part of Ser. No. 679,357, Apr. 22, 1976, abandoned, which is a continuation-in-part of Ser. No. 518,875, Oct. 29, 1974, Pat. No. 4,045,565.

[30] Foreign Application Priority Data

Oct. 29, 1973 [FR] France .................................. 73 38416

[51] Int. Cl.$^3$ ............................................ C07D 471/02
[52] U.S. Cl. ................................................ 546/70
[58] Field of Search ......................................... 546/70

[56] References Cited

U.S. PATENT DOCUMENTS 3,933,827  1/1976  Bross et al. ............................ 546/70

FOREIGN PATENT DOCUMENTS 52-23098  2/1977  Japan ..................................... 546/70

Primary Examiner—Glennon H. Hollrah
Assistant Examiner—D. B. Springer
Attorney, Agent, or Firm—Charles H. Lindrooth; Alexis Barron; Martin F. Savitzky

[57] ABSTRACT

Derivatives of 9-hydroxy ellipticine, preparation thereof, and use thereof for the treatment of leukemias and solid tumors.

11 Claims, No Drawings

SYNTHESIS OF PYRIDO[4,3-B]CARBAZOLE DERIVATIVES

This is a division of application Ser. No. 942,793, filed Sept. 15, 1978, now U.S. Pat. No. 4,310,667 which is a continuation-in-part of Ser. No. 679,357, filed Apr. 22, 1976, now abandoned, which is a continuation-in-part of Ser. No. 518,875, filed Oct. 29, 1974, now U.S. Pat. No. 4,045,565.

This invention relates to new products, namely 2-N-quaternized derivatives of 9-hydroxy-ellipticine, i.e. 2-N-quaternized derivatives of 9-hydroxy-5,11-dimethyl-(6H) pyrido[4,3-b]carbazole, and methods for obtaining same. The invention further relates to the application of said compounds as a medicine or as the active principle of pharmaceutical compositions, notably for the treatment of cancers. The compounds of the invention have been shown to be exceptionally efficacious in the treatment of different forms of cancer.

The preparation and therapeutic application of 9-hydroxy-ellipticine (9—OH—E) have been described in said U.S. Pat. No. 4,045,565, which is hereby incorporated by reference and made a part hereof. The preparation and therapeutic application of an ellipticine derivative, 9-methoxy-ellipticine lactate, has also already been described. Recent studies described in an article by G. MATHE et al. in Rev. Europ. Etudes Clin. Biol. 15, 1970, pp. 541–545 and in an article by J. LE MEN et al in the above mentioned review pp. 534–538, have shown that 9-methoxy-ellipticine lactate, apart from an oncostatic action in mouse L 1210 leukemia and BP 8 tumors, is effective in acute myeloblastic leukemia, but has been found to be ineffective in the treatment of acute lymphoblastic leukemia and Hodgkin's disease; moreover, although it has an immunosuppressive action when administered after the antigen, 9-methoxy-ellipticine lactate does not reveal such an activity when administered to humans. 9-methoxy-ellipticine is an essential alkaloid of Ochrosia leaves.

Furthermore, both 9-methoxy-ellipticine and other compounds commonly used in human therapeutics for the treatment of certain tumors, such as, for example, bis-betachloroethyl nitroso urea, Amethopterin or Methotrexate, 6-mercapto-purine, 5-fluoro-uracile or cyclophosphamide or Endoxan, only reveal substantial antitumor activity at strong doses close to the lethal dose or LD 50. But it would, on the contrary, be very advantageous, notably in human therapeutics, to be able to administer the active antitumor principles at doses as far removed as possible from the toxic doses.

New compounds derived from 9-hydroxy-ellipticine have now been found which have considerably higher antitumor properties with respect to many tumors and particularly with respect to mouse L 1210 leukemia and mouse P 388 leukemia, compared with those of the above-mentioned known compounds, including 9-hydroxy-ellipticine.

The new compounds of the invention are the water soluble 2-N quaternary salts of a compound of the formula:

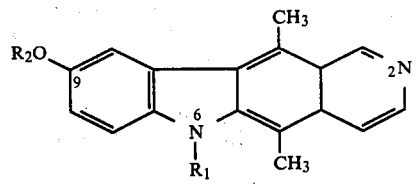

wherein $R_1$ is selected from the groups consisting of hydrogen and alkyl groups and $R_2$ is selected from the groups consisting of hydrogen, alkyl and acyl groups.

These compounds can also be described as being more specifically the water soluble 2-N quaternary salts having the formula:

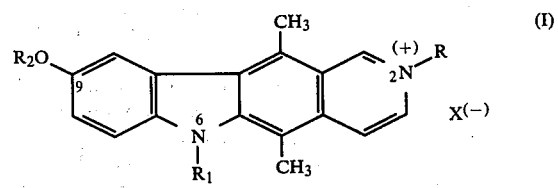

wherein $R_1$ and $R_2$ are as above defined, and R is an alkyl group selected from the groups consisting of purely alkyl groups and substituted alkyl groups. Whereas $X^{(-)}$ is an appropriate quaternizing anion.

By substituted alkyl groups, it should be intended preferably alkyl groups substituted by one or two hydroxy groups, and alkyl groups substituted by an amino group, which in turn is preferably substituted by alkyl groups or the nitrogen atom of which is part of a heterocycle. More preferred compounds of this invention are those wherein:

$R_1$ is H, $CH_3$ or $C_2H_5$
$R_2$ is H, $CH_3$, $C_2H_5$, $C_6H_5CH_2-$, $CH_3CO-$, $C_6H_5-CO-$.
R is $CH_3$, $C_2H_5$, $C_2H_4OH$, $C_3H_6OH$, $C_3H_5(OH)_2$,

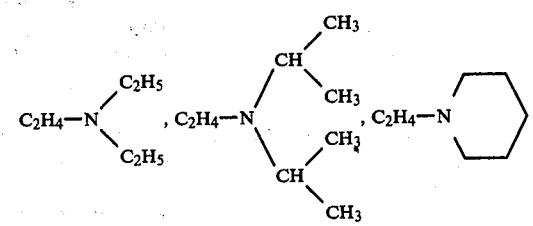

X is an acyloxy group, and most preferably $CH_3COO$.

Specific compounds corresponding to formula I above are the following:
9-hydroxy-2-methyl-ellipticinium acetate,
9-hydroxy-2-ethyl-ellipticinium acetate,
9-hydroxy-2-hydroxyethyl-ellipticinium acetate,
9-hydroxy-2-hydroxypropyl-ellipticinium acetate,
9-hydroxy-2-dihydroxypropyl-ellipticinium acetate,
9-hydroxy-2($\beta$-diethylamino-ethyl)-ellipticinium acetate,
9-hydroxy-2($\beta$-diisopropylamino-ethyl)-ellipticiniu acetate,
9-hydroxy-2($\beta$-piperidino-ethyl)-ellipticinium acetate,
9-methoxy-2-methyl-ellipticinium acetate,
9-acetoxy-2-methyl-ellipticinium acetate,
9-acetoxy-2-ethyl-ellipticinium acetate,
9-benzyloxy-2-methyl-ellipticinium acetate, 9-benzyloxy-2-ethyl-ellipticinium acetate,
9-hydroxy-2,6-dimethyl-ellipticinium acetate,
9-hydroxy-6-methyl-2-ethyl-ellipticinium acetate,
9-hydroxy-6-methyl-2-hydroxyethyl-ellipticinium acetate,
9-hydroxy-2,6-diethyl-ellipticinium acetate,
9-hydroxy-6-ethyl-2-hydroxyethyl-ellipticinium acetate,
9-ethoxy-2,6-diethyl-ellipticinium acetate,
9-ethoxy-6-ethyl-2-(β-hydroxy-ethyl)-ellipticinium acetate,
9-benzoyloxy-2,6-dimethyl-ellipticinium acetate, and
9-benzoyloxy-6-methyl-2-ethyl-ellipticinium acetate, among others.

Said compounds can be prepared, either directly or indirectly, from 9-hydroxy-ellipticine, the formula of which together with its characteristics, and a process for preparing it, were described in U.S. Pat. No. 4,045,565, incorporated herein by reference.

A process for the preparation of said compounds comprises the conversion of 9-hydroxy-ellipticine into a 9-hydroxy-2-alkyl-ellipticinium halide (which could also be named a 9-hydroxy-ellipticinium haloalkylate) and eventually the preparation of the 9-hydroxy-2,6-dialkyl-ellipticinium halide by using an appropriate alkyl halide, and the conversion of the same into the corresponding water soluble salt by known means.

According to a preferred embodiment, the compounds of this invention, especially the compounds having the 2,6, and 9-positions substituted, are prepared by a total synthesis, on which details are given hereinbelow.

But for the embodiment comprising use of 9-hydroxy-ellipticine as the starting material, it is possible to prepare the starting 9-hydroxy-ellipticine as described in the aforesaid U.S. Patent, that is to say by demethylation of 9-methoxy-ellipticine with, for example, pyridine hydrochloride glacial acetic acid saturated with hydrochloric acid, gaseous hydrobromic acid or hydroiodic acid. It is, however, preferable to effect the demethylation of 9-methoxy-ellipticine in the presence of recrystallized pyridine hydrochloride in distilled pyridine as, with said demethylation agent, a pure 9-hydroxy-ellipticine is obtained, i.e., free of undesirable by-products.

The demethylation agent should preferably be used in a large molar excess based on the moles of 9-methoxy-ellipticine used.

The starting 9-methoxy-ellipticine can be obtained by extraction from a natural source, or by synthesis (with respect to this see, among others, the articles by J. W. LODER in Aust. J. Chem. 1967, 20, pp. 2715–2727 and J. POISSON and C. MIET in Ann. Pharm. Franc. 1967, 25; p. 523).

But as explained above, the best mode of preparation of the compounds of this invention, especially of those which are substituted on the 2,6 and 9-positions, is constituted by a novel synthesis, which is also part of this invention. The method used for this synthesis comprises the steps essentially consisting of condensing 5-methoxy-indole on hexane-2,5-dione for preparing 6-methoxy-1,4-dimethyl-carbazole, dimethylating the said 6-methoxy-1,4-dimethyl-carbazole for preparing 6-hydroxy-1,4-dimethyl-carbazole, protecting the hydroxy radical of the latter by benzoylating the said 6-hydroxy-1,4-dimethyl-carbazole, metallating the 6-benzoyl-oxy-1,4-dimethyl-carbazole thus prepared and treating the metallated product by alkyl iodide for preparing 9-alkyl-6-benzoyl-oxy-1,4-dimethyl-carbazole, formylating the latter for preparing 3-formyl-9-alkyl-6-benzoyl-oxy-1,4-dimethyl-carbazole, condensing the said 3-formyl-9-alkyl-6-benzoyl-oxy-1,4-dimethyl-carbazole with the dimethyl-acetal of aminoacetaldehyde for preparing 3-(β,β-dimethoxy-ethyl-imino-methyl)-9-alkyl-6-benzoyl-oxy-1,4-dimethyl-carbazole, cyclising the latter and saponifying the 9-benzoyl-oxy-6-alkyl-ellipticine thus prepared for obtaining 9-hydroxy-6-alkyl-ellipticine, treating the same with an alkyl halide for preparing a 9-hydroxy-2,6-dialkyl-ellipticinium halide, and, if desired, converting the said substituted ellipticinium halide into a corresponding 9-hydroxy-2,6-dialkyl-ellipticinium water soluble 2-N-quaternary salt.

It should be noted that the alkyl halide used for the alkylation on the 2-position of the ellipticinium structure can be either a purely alkyl group-containing halide or a substituted alkyl group-containing halide appropriate for introducing a substituted alkyl group R as above defined.

The corresponding reaction schemes are given with more details hereafter:

1-Preparation of 6-methoxy-1,4-dimethyl-carbazole, by condensation of 5-methoxy-indole with hexane-2,5-dione in toluenic medium, with p-toluene-sulfonic acid (PTSA) as a catalyst.

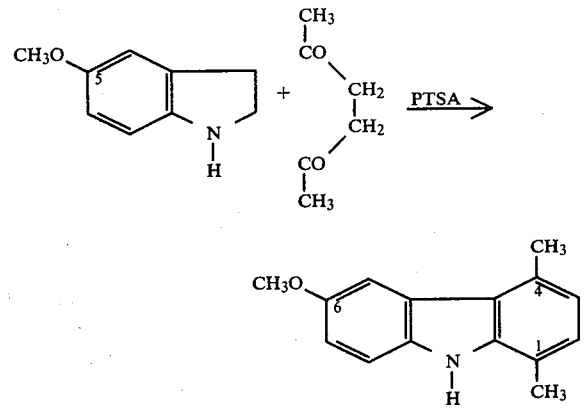

2-Preparation of 6-hydroxy-1,4-dimethyl-carbazole, by demethylation using pyridinium chloride, especially prepared therefor and used both as demethylating agent and as solvent.

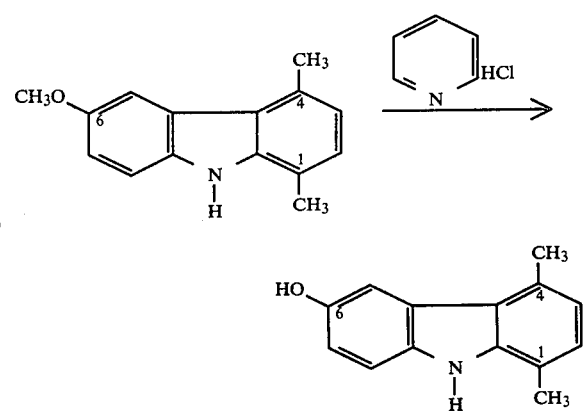

3-Protection of the hydroxy group by preparation of the 6-benzoyl-oxy-1,4-dimethyl carbazole, by reaction of the 6-hydroxy-1,4-dimethyl-carbazole, dissolved in pyridine or in acetone, with benzoyl chloride (freshly rectified), in the presence of tri-ethylamine.

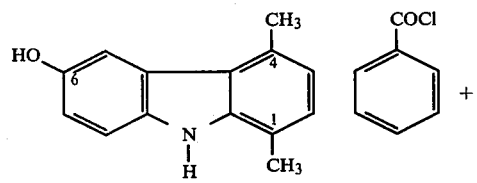

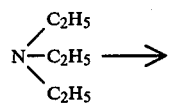

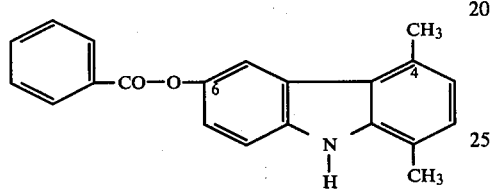

4-Preparation of 9-alkyl-6-benzoyl-oxy-1,4-dimethyl-carbazole, by metallation of 6-benzoyl-oxy-1,4-dimethyl-carbazole, dissolved in DMF with NaH and treatment of the sodium containing derivative with an alkyl iodide I-R (e.g. methyl iodide, ethyl iodide, etc.).

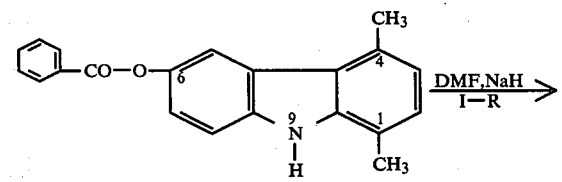

R=CH$_3$, C$_2$H$_5$ or more generally an alkyl group, e.g. a C$_1$-C$_3$ alkyl group.

5-Preparation of 3-formyl-9-alkyl-6-benzoyl-oxy-1,4-dimethyl-carbazole, in an "ortho-dichloro-benzenic" medium by means of N-methyl formamilide in the presence of phosphorus oxychloride.

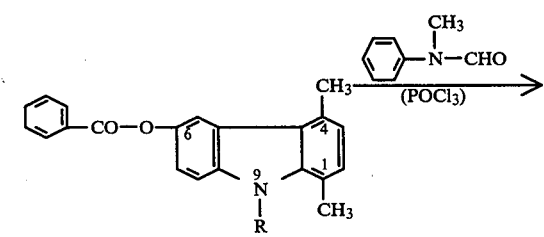

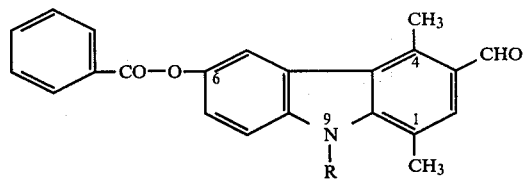

6-Preparation of 3-($\beta$,$\beta$-dimethoxy-ethyl-imino-methyl)-9-alkyl-6-benzoyl-oxy-1,4-dimethyl-carbazole, by condensation of the product of step 5 with amino-acetaldehyde dimethyl-acetal.

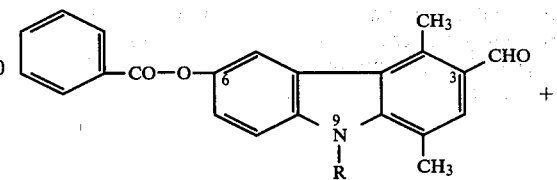

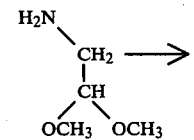

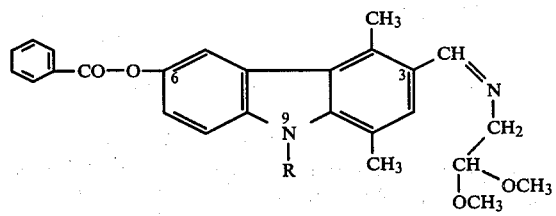

7-Preparation of 9-benzoyl-oxy-6-alkyl-ellipticine (base), by cyclisation of the azo-methine thus obtained, in the presence of a mixture of 91% phosphoric acid and of phosphorus pentoxyde.

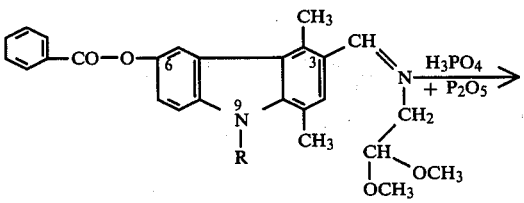

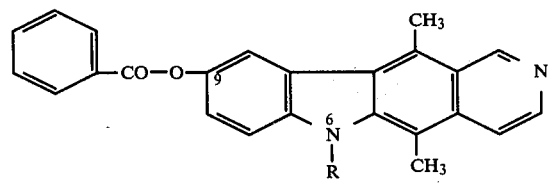

8-Preparation of 9-hydroxy-6-alkyl-ellipticine (base), by saponification of the latter ester in an alkaline medium or in an acid medium:

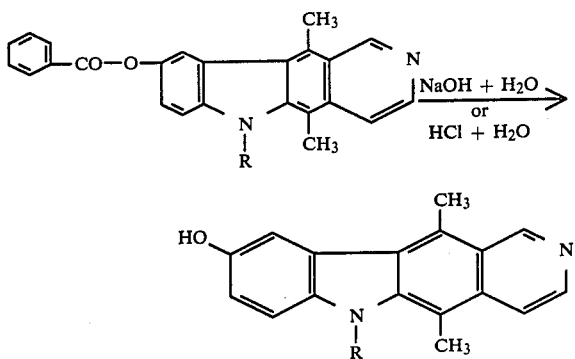

9-Preparation of the 9-hydroxy-2,6-dialkyl-ellipticinium halide (or haloalkylate of 9-hydroxy-6-alkyl-ellipticinium), by reaction of the product of step 8 with an alkyl halide, e.g. methyl iodide or ethyl iodide, in DMF medium.

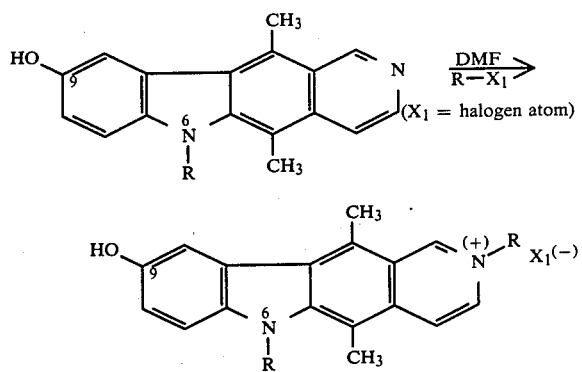

The product thus obtained is practically insoluble into water, but soluble into DMF.

10. Preparation of the water soluble 2-N-quaternary salt of this invention, by conversion into a water soluble salt of the said halide obtained in step 9; according to a most preferred (but not at all limitative) embodiment, said halide of step 9 can be converted into the corresponding acetate, advantageously by a conventional means such as an appropriate ion exchange resin.

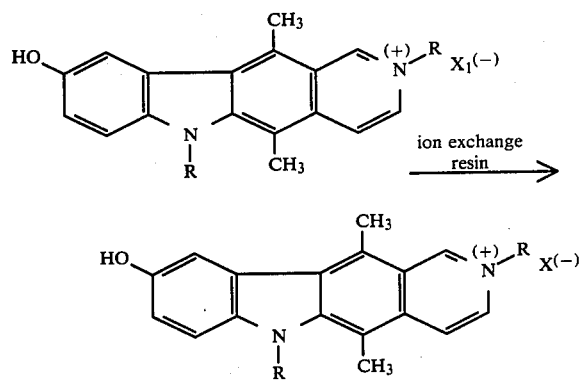

(e.g. X=CH₃COO).

Examples of ion exchange resins which may be used therefore are those which are known and available under the trade names of Amberlite and Bio-Rad (Analytical Grade Anion Exchange Resin Bio-Rad, Ag$^R$ 1—X8, in the acetate form, marketed by Bio-Rad Laboratories, Richmond, Calif., USA).

It must be noted that both these halides and acetates thus obtained in steps 9 and 10 respectively decompose before melting, so that they have no distinct melting point. But they can be distinguished from each other by elementary analysis, by their differences of solubility in DMF or in water, by analytical control of the absence of halogen atoms (for the acetate form), and preferably by high performance liquid chromatography, all these techniques being well known by those with ordinary skill in the art.

Another object of the invention is an anticancer pharmaceutical composition including a therapeutically effective amount of at least one 2-N quaternary salt as described above; the said composition can, for example, be in the form of an injectable solution or solid preparation, especially for a percutaneous treatment or for an administration per os.

Still another object of this invention is a method of cancer treatment comprising using by known means a therapeutically effective amount of at least one water soluble ellipticinium salt as defined above.

The compounds of the invention, and more particularly the water soluble acetate have unexpectedly appeared to be exceptionally effective in the treatment of cancer. This efficacy is such that it enables 99.999% of leukemia cells to be destroyed for an inoculum of $10^5$ mouse L 1210 leukemia cells, even though the doses necessary to obtain this result are very substantially below the lethal dose, which is very advantageous both from the medical and economic standpoints.

The effect the compounds of the invention have on mouse L 1210 or P 388 leukemias was used to test the antitumor activity of said compounds.

The experimental tumor mouse L 1210 leukemia is commonly used to evaluate the effects of all the antitumor compounds now used in human therapeutics, as was described, for example, by C. C. ZUBROD in Proc. Nat. Acad. Sci. USA 69, 1972, pp. 1042–1047. This experimentally formed tumoral system permits very accurate quantitative evaluation of the activity of the compound tested and also, consequently, an objective comparison of the respective activities of various compounds, for example, according to the methods described by H. E. SKIPPER, F. M. SCHABEL Jr. and W. S. WILCOX in Cancer Chemiother. Rep. 1964, pp. 1–111 and 45, 1965, pp. 5–28.

In practice, mice having received an intraperitoneal injection of an inoculum of L 1210 leukemia cells were used, half of them having been subjected to an intraperitoneal injection of a single dose of one of the compounds to be tested 24 hours after the said tumoral inoculation; the other half of the mice received an injection of an identical volume of an inactive solvent and were used as a control series. The mice were randomized in each experimental series. A first routine experiment enable the death rate by toxicity to be determined and thus established the sublethal doses.

According to the convention in force in this field, the animals which survived longer than 45 days after inoculation of tumoral cells were considered to be cured.

It was thus possible to determine the death rate due to toxicity resulting from a single injection of different doses of one of the compounds (sublethal doses, LD 50 and LD 100) and to evaluate the survival rate of the group of animals which had only been injected with a sublethal dose of a compound of the invention.

The survival rate was calculated from a statistical analysis of: the experimental results, compared with the results obtained with the control series, according to the well known Mann-Whitey and Wilcoxon Methods; the percentage of leukemic cells killed by the treatment applied was calculated by the method described by H. E. Skipper et al in the above-mentioned articles, taking as a basis either the increase in the mean survival in the absence of survivors, or the percentage of survivors, as the case may be.

To evaluate the therapeutic activity of the compounds of the invention, doses of said compound were expressed basing them on the 30 days sublethal dose which was fixed at 1. Said sublethal dose was in fact easier to determine for the compounds of the invention than the LD 10 which it approximates very closely and which is usually taken as a reference for the evaluation of the therapeutic activity of compounds having an antitumor effect (see H. E. Skipper et al, articles mentioned above).

The therapeutic activity on mouse P 388 leukemia is comparable to that obtained on L1210 leukemia for the same doses, using the same procedure.

It was thus possible to determine that the compounds of the invention, notably in the form of the acetate at doses very much lower than the lethal dose, make it possible to kill up to 99.999% of leukemic cells for an inoculum of $10^5$ cells of mouse L1210 leukemia, which is very exceptional, compared with the results obtained with the above-mentioned products now commonly used in human therapeutics.

Now, it is naturally advantageous to be able to use such active compounds, notably in human therapeutics at doses as far removed as possible from toxic doses.

It appeared that, as a general rule, the 2-(N)quaternized compounds of this invention display a somewhat higher general toxicity in mice than their non quaternized counterparts ($DL_O$ between 0.5 and 10 mg/kg after a single i.p. injection). However, they are endowed with a better chemotherapeutic index on L 1210 leukemia; several of them are still active at a dose lower than $(1 \times 100) \times DL_O$. The quaternization resulted in a 4-10 fold reduction of the effects of these drugs on the rate of L1210 cells multiplication in vitro; the drug concentrations which inhibit by 50% this rate are in the 10-100 mg/ml range.

The methyl 2-(N)compounds are not glucuroconjugated and no metabolite has been found. The quaternized ellipticine derivatives of this invention proved to be unable to bind on microsomal hydroxylases and are therefore not mutagenic on Ames Salmonella test, contrary to most nonquaternized ellipticine derivatives which bind strongly to the oxidized and reduced liver microsomal cytochromes P-450 of differently pretreated rats, producing typical difference spectra, with peaks respectively at 428 and 445 nm (spectral dissociation constants around $10^{-6}$–$10^{-7}$M and $10^{-5}$M, respectively). These 2-(N)-methyl-compounds are neither capable to inhibit benzo(a)pyrene hydroxylase or to hinder the microsomal formation of water soluble metabolites of the hydrocarbon and its covalent binding to DNA. The last two properties are characteristics of the non quaternized ellipticines.

The simplest derivative in this series is the 2-(N)methyl 9—OH—ellipticinium(2-N$^+$CH$_3$—9—OH—E). It is much more active than 9—OH—E on several mouse and rat tumors, as shown by the comparative test results gathered in table I hereafter.

TABLE I

Effect of 9-OH—E and its 2N$^+$CH$_3$ derivative on experimental tumors

| Tumor | 9-OH—E | 2N$^+$CH$_3$-9-OH—E |
|---|---|---|
| Mice | | |
| Leukemia L1210 | + | ++ |
| Leukemia P 388 | + | ++ |
| Lewis lung carcinoma | ± | ± |
| Myeloma (ADJ-PCGA) | + | |
| Osteosarcoma | | |
| Ependymoblastoma | | |
| Melanoma B16 | + | ++ |
| Rats | | |
| Yoshida lymphosarcoma (in vitro) | | ++ |
| Gardner lymphosarcoma OG | | ++ |
| Squamous-cell carcinoma | | + |
| EHTH mycloid leukemia | | – |

Moreover, contrary to 9—OH—E, it is active on some human tumors. A phase I trial was done at the Cancer Institute of 14-Caen, France. A weekly dose in the range of 50 to 100 mg per m2 was given intravenously over a 30 minutes period to patients refractory to usual chemotherapeutic or radiotherapeutic treatments (3). Eight of the first 18 patients underwent subjective or objective improvements. They were suffering from advanced breast, thyroid, or colon cancers, with bone or lung metastasis in mostcases. No major toxic side effects were recorded.

Again, these drugs are better tolerated by humans than by animals; they are devoid of any hematological toxicity; and autoradiographic studies have shown that they are unable to penetrate into bone marrow in significant amounts. Preclinical studies are now underway with other quaternarized 9—OH—E of higher molecular weight. The ethyl compounds are the most active ones in this series as judged by their action on L1210 leukemia. The best ethyl compounds were selected according to four criteria (see table II)hereinbelow): (i) increased life span (ILS) higher than 100% after intraperitoneal injection of $10^5$ cells; (ii) occurrence of cured animals; (iii) chemotherapeutic index better than 50; and (iv)persistence of the antileukemic action even after an intravenous injection. Two of these products will be submitted to clinical trials.

To understand the increase of the antitumor efficiency of the quaternarized compounds, several parameters of action of 9—OH—E and its methyl derivative have been comparatively established (see table III). Both compounds have about the same affinity for DNA. On a weight basis, the methyl compound is about 10 times more toxic in mice but also 10 times more efficient on leukemic mice (ILS). Surprisingly, the same derivative is four times less active than 9—OH—E on the rate of growth of L1210 cells in vitro. Therefore, there is no quantitative parallel between the in vivo and in vitro action of these drugs. The N-quaternization markedly changes the biodisponibility of the drugs as shown by autoradiography with $^{14}$C-labeled molecules. Whereas the 9—OH derivative concentrates in several organs, including the lungs and the pancreas, and is mostly eliminated through the bile into feces, the methyl derivative is devoid of any ability to concentrate in lungs and pancreas; its elimination through feces is reduced, but it displays the capacity to concentrate in the intestinal walls and in the thyroid. These data provided useful guidelines for clinicians. Several ellipticine derivatives are mutagenic on Ames Salmonella test; however, the quaternized derivatives lose this property. The microsomes, which are able to metabolize some ellipticines, increase the mutagenic ability of these drugs in vitro. Again, the quaternized compounds do not show any mutagenicity in the presence or absence of the microsomal enzymes. According to these results, a study on the enzymatic transformation of some ellipticine derivatives by microsomal enzymes in vitro has been completed. Due to the curved shape of their molecules, their relative hydrophobicity, and the presence of a heterocyclic nitrogen, the ellipticines are good substrates for the cytochrome P450 system, provided that the 2-N remains uncharged.

Metabolic studies in mice have established that ellipticine itself is hydroxylated in the 9-position and then glucuroconjugated and that 9—OH—E is only glucuroconjugated, whereas the 2N+CH$_3$—9—OH—E is excreted with no major modification. Since the quaternized compound is still highly active as an antitumor agent, it can be concluded that the liver microsome enzymes, which are responsible of the major features of ellipticine metabolism, do not intervene in the expression of the antitumor properties.

In conclusion, it appears that the quaternization of the ellipticines leads to at least three main changes in the properties of these molecules: (i) they are more effective as antitumor agents and give encouraging preliminary results in humans; (ii) their biodisponibility is greatly modified; and (iii) their metabolic transformation is hindered.

TABLE II

EFFECTIVENESS OF SOME $N_2$—ethyl ellipticines on L1210 leukemia in vivo

| $R_9$ | $R_6$ | $R_2$ | Activity ILS ≧ 100% | IP route Surviving to D < $LD_o$ | Chemotherapeutic index: $\frac{LD_o}{D_{ILS} \simeq 25\%} \geqq 50$ | IV route (ILS ≧25%) |
|---|---|---|---|---|---|---|
| —H | —H | —H | + (119 to $LD_o$/5) | + (3/20 to $LD_o$/5) | +75 | + |
| CH$_3$—C(=O)— | —H | —H | | + (3/20 to $LD_o$/3) | +100 | |
| —H | —CH$_3$ | —H | + (102 to ≃ $LD_o$/2) | | | |
| —H | —H | —OH | + (117 to $LD_o$/2) | + (2/15 to $LD_o$/2) | | + |
| —H | —H | —N(CH$_2$—CH$_3$)$_2$ | | + (6/20 to $LD_o$/2) | +100 | |
| —H | —H | —N(CH$_2$—CH$_2$)$_2$CH | | | | + |
| —H | —H | —N(CH$_2$—CH$_2$)$_2$CH$_2$ | + (102 to $LD_o$/5) | + (5/15 to $LD_o$) | +100 | + |

TABLE III

In vitro and in vivo comparative effects of 9-OH—E and its $N_2$—CH$_3$ derivative

| | | L 1210 cells | | | |
|---|---|---|---|---|---|
| Compound | DNA affinity (10$^6$ M$^{-1}$) | In vivo dose (mg/kg) to reach ILS 25% | In vitro ID$_{50}$ mg/ml | 10$^{-M}$ | $LD_o^x$ (mg/kg) for mice |
| 9-OH—E | 2.3 | 10 | 4.3 | 1.6 | 50 |
| 2N+CH$_3$—9-OH—E | 1.3 | 1 | 15.5 | 5.6 | 5 |

$^x$Highest non lethal dose.

On the other hand, the 2-N quaternary units of this invention in the form of the acetate showed a marked antalgic activity on mice, as well as important anti-inflammatory and cardiovascular activities on dogs.

The invention is further illustrated by the following examples, which are illustrative of this invention rather than restrictive of its scope. In these examples, the expressions "iodomethylate" and "iodoethylate" are to be considered as mere equivalents of "2-methyliodide and" 2-ethyl iodide" respectively. Unless otherwise specified, the percentages given in these examples are in weight.

EXAMPLE 1

9-hydroxy-ellipticinium iodomethylate (or 9-hydroxy-2-methyl-ellipticinium iodide)

(a) Preparation of 9-hydroxy-ellipticine

A mixture of one part by weight 9-methoxy-ellipticine obtained by extraction from "yellowwood" (Ochrosia maculate)from the island of Reunion, and from 3 to 11 parts by weight of pyridine hydrochloride, were heated with gentle reflux for 30 to 90 minutes. The reaction mass became a dark brown colour; it was then poured over crushed ice, the precipitate formed was centrifuged and washed several times with iced water and then recrystallized in methanol. The crystals obtained were orange coloured.

The melting point of the crystalline product was substantially higher than 330° C. The empirical formula of said product, which it was established crystallized with 1 mole methanol, was $C_{18}H_{18}N_2O_2$, which gave the empirical formula $C_{17}H_{14}N_2O$ for pure 9-hydroxy-ellipticine; the molecular weight of the latter being 262, elementary analysis gave:

|  | C % | H % | N % | O % |
|---|---|---|---|---|
| calculated | 73.53 | 5.17 | 9.53 | 10.88 |
| found | 73.50 | 5.35 | 9.48 | 10.84 |

At $3100^{cm-1}$, the IR spectrum of the compound gave the line characteristic of the —OH group.

Its mass spectrum revealed a M+ 262 molecular peak and analysis with thin layer chromatography using alumina as a substrate and a 28:2 benzene:ethanol mixture as eluant gave a Rf of 0.44.

(b) Preparation of 9-hydroxy-ellipticinium iodomethylate 1 g 9-hydroxy-ellipticine was dissolved in 10 ml pure, anhydrous dimethylformamide and 3 g methyl iodide was added. The mixture was left to stand for several hours; the precipitate was centrifuged and washed with anhydrous ether.

The crystalline product obtained consisted of fine, bright orange-yellow crystals which did not melt at 330° C. It gave a positive result when subjected to a halogen test (copper wire in a flame).

The empirical formula of said compound was $C_{18}N_{17}N_2O$ I, the molecular weight being 404.248; elementary analysis gave:

|  | C % | H % | N % | I % |
|---|---|---|---|---|
| calculated | 53.48 | 4.25 | 6.93 | 31.39 |
| found | 53.78 | 4.30 | 6.89 | 31.20 |

EXAMPLE 2

9-hydroxy-ellipticinium iodoethylate (or 9-hydroxy-2-ethyl-ellipticinium iodide)

The same procedure was used as in example 1-b) but using a molar excess of ethyl iodide, instead of 3 g of methyliodide.

The empirical formula of the compound obtained being $C_{19}H_{19}N_2OI$ and the molecular weight 418.27, elementary analysis gave:

|  | C % | H % | N % | I % |
|---|---|---|---|---|
| calculated | 54.55 | 4.58 | 6.70 | 30.34 |
| found | 54.42–54.50 | 4.48–4.55 | 6.63–6.65 | 30.22 |

EXAMPLE 3

9-acetoxy-ellipticine 1 g of 9-hydroxy-ellipticine was dissolved in 20 ml pyridine dried on potash and a solution of 3 g acetic anhydride in 10 ml pyridine was added with magnetic stirring.

The orange coloured solution first darkened and then became a clear red. It was diluted with water and a precipitate then formed, which was centrifuged and dissolved in $CHCL_3$. The chloroformic solution was washed with water; it was dried on $Na_2SO_4$ filtered, and the solvent was expelled. Recrystallization was effected in benzene and 1 g of product was obtained, consisting of fine yellow crystals melting at 282° C.

Analysis by thin layer chromatography using Silicagel as a substrate and a 24:6 benzene:ethanol mixture as eluant gave a Rf of 0.40.

The empirical formula of said compound being $C_{19}H_{16}N_2O_2 + \frac{1}{2}H_2O$ and its molecular weight 304.33+9=313.33, elementary analysis gave:

|  | C % | H % | N % |
|---|---|---|---|
| calculated | 73.14 | 5.47 | 8.98 |
| found | 73.07–73.21 | 5.73–5.75 | 8.65–8.81 |

A further analytic check was carried out and a differentation of 9-hydroxy-ellipticine and 9-acetoxy-ellipticine. The results are given in the following table.

|  | Test with $FeCl_3$ | UV detection 320–380 nm fluorescence | Detection with iodine vapor |
|---|---|---|---|
| 9-hydroxy-ellipticine | positive | No fluorescence | red |
| 9-acetoxy-ellipticine | negative | yellow fluorescence | brown |

Preparation of the 9-acetoxy ellipticine hydrochloride

A 9-acetoxy-ellipticine solution (base) dissolved in pure, anhydrous dimethylformamide, was treated with an etheral solution of gaseous hydrochloric acid. A precipitate formed, which was centrifuged, washed with anhydrous ether and recrystallized in absolute ethanol, and precipitated again with anhydrous ether.

The fine yellow crystals which formed decomposed and charred, without melting, at about 300° C. Said compound had the empirical formula $C_{19}H_{16}N_2O_2, \frac{1}{2}H_2O, HCl$.

EXAMPLE 4

9-acetoxy-ellipticinium iodomethylate (or 9-acetoxy-2-methyl-ellipticinium iodide)

1 g of 9-acetoxy-ellipticine (base) was dissolved in 10 ml pure, anhydrous dimethylformamide. 3 g of methyl iodide was added with magnetic stirring. Three hours later, the precipitate formed was centrifuged and washed with anhydrous ether. Fine yellow crystals were obtained having a melting point >330° C.

The empirical formula of the compound being $C_{20}H_{19}N_2O_2I$ and its molecular weight 446.286, elementary analysis gave:

|  | C % | H % | N % | I % |
|---|---|---|---|---|
| calculated | 53.82 | 4.29 | 6.28 | 28.52 |
| found | 53.70–53.92 | 4.15–4.18 | 6.30–6.35 | 28.45 |

EXAMPLE 5

9-acetoxy-6-methyl-ellipticine (base)

1 g of 9-acetoxy-ellipticine was dissolved in 10 ml pure, anhydrous dimethylformamide (on molecular sieve). 0.1 g sodium hydride (as a 50% suspension in oil) previously washed several times with anhydrous ether was added.

0.453 g of methyl iodide was introduced with magnetic stirring and at room temperature.

After stirring for 30 minutes, the solution was diluted with water and extracted twice with $CHCl_2$ (25 ml each time). The chloroformic solution was washed with water and then dried on $Na_2SO_4$; then, the product was filtered and the solvent expelled.

The product was recrystallized in a mixture of 1 volume ethanol and 4 volumes benzene and fine yellow crystals were obtained.

Analysis by thin layer chromatography using silicagel as substrate and a 24:6 benzene:ethanol mixture as eluant gave a Rf of 0.50.

The empirical formula of said compound being $C_{20}H_{18}N_2O_2$ and its molecular weight 318.378, elementary analysis gave:

|  | C % | H % | N % |
|---|---|---|---|
| calculated | 75.46 | 5.70 | 8.80 |
| found | 75.42–75.38 | 5.75–5.82 | 8.63–8.50 |

EXAMPLE 6

9-acetoxy-6-methyl-ellipticinium iodomethylate (or 9-acetoxy-2,6-dimethyl-ellipticinium iodide)

1 g of 9-acetoxy 6-methyl-ellipticine (base) was dissolved in 10 ml pure, anhydrous dimethylformamide, 3 g of methyl iodide was added and the solution was left to stand for 3 hours.

The precipitate was centrifuged and washed with anhydrous ether. The compound obtained consisted of fine yellow crystals which did not melt at 330° C., but decomposed at about 335° C.

The empirical formula of said compound being $C_{21}N_{21}N_2O_2I$ and its molecular weight being 460.313, elementary analysis gave:

|  | C % | H % | N % | O % | I % |
|---|---|---|---|---|---|
| calculated | 54.83 | 4.60 | 6.09 | 6.96 | 27.59 |
| found | 54.66 | 4.56 | 5.88 | 7.22 | 27.48 |

EXAMPLE 7

9-hydroxy-6-methyl-ellipticine (base)

1 g of 9-acetoxy 6-methyl-ellipticine (base) was dissolved in 10 ml absolute ethanol. A few drops of caustic soda of density d: 1.33 were added with magnetic stirring until pH 9 was obtained.

Stirring was continued for a further 30 minutes. The solution was precipitated with anhydrous ether; after centrifugation, the product was washed with ether and yellow crystals were obtained having a melting point of 314°–315° C.

The empirical formula of said compound being $C_{18}H_{16}N_2O$ and its molecular weight being 276.32, elementary analysis gave:

|  | C % | H % | N % | O % |
|---|---|---|---|---|
| calculated | 78.25 | 5.83 | 10.13 | 5.79 |
| found | 78.20–78.08 | 5.75–5.65 | 10.06 | 5.55 |

A further analytic verification was also effected, as was differentiation, between 9-acetoxy-ellipticine, 9-acetoxy 6-methyl ellipticine and 9-hydroxy 6-methyl-ellipticine. The results are given in the following table:

| TLC(Silicagel) benzene:ethanol 26:4 | Test with $FeCl_3$ | UV detection 320–380 nm fluorescence | detection with iodine vapour |
|---|---|---|---|
| 9-acetoxy-ellipticine | negative | yellow fluorescence | brown |
| 9-acetoxy 6-methyl ellipticine | negative | yellow fluorescence but migrates higher | brown |
| 9-hydroxy 6-methyl ellipticine | positive | no fluorescence but same Rf as 9-acetoxyellipticine | dark brown |

EXAMPLE 8

9-hydroxy-6-methyl-ellipticinium iodomethylate (or 9-hydroxy-2,6-dimethyl-ellipticinium iodide)

1 g of 9-hydroxy 6-methyl-ellipticine (base) was dissolved in 10 ml pure, anhydrous dimethyl formamide; 3 g methyl iodide was added with magnetic stirring, which was continued for 2 hours. The precipitate formed was then centrifuged and washed with anhydrous ether, fine yellow crystals being obtained having a melting point higher than 330° C.

The empirical formula of the compound being $C_{19}H_{19}N_2OI$ and its molecular weight 418.26, elementary analysis gave:

|  | C % | H % | N % | I % |
|---|---|---|---|---|
| calculated | 54.59 | 4.57 | 6.69 | 30.34 |
| found | 54.90–55.01 | 4.64–4.59 | 6.31–6.39 | 30.20 |

EXAMPLE 9

The general procedure of example 1 was followed, but using the respective appropriate reactants in each case, and the following compounds were obtained:

9-hydroxy-6-methyl-2-ethyl-ellipticinium iodide: $C_{20}H_{21}N_2OI$

Molecular weight: 432

|  | C % | H % | N % | O % | I % |
|---|---|---|---|---|---|
| calculated | 55.61 | 4.90 | 6.48 | 3.70 | 29.38 |
| found | 55.63 | 4.94 | 6.57–6.25 | 3.85 | 29.52 |

(by thin layer chromatography(TLC); Silicagel Merck F-254; solvent:mixture 4/1/5 of butanol/acetic acid/water).

9-hydroxy-6-methyl-2-ethyl-ellipticinium acetate:
(obtained by exchange of the previous one on a Bio-Rad ® resin in the acetate form, in DMF).
$C_{22}H_{24}N_2O_3$
Molecular weight: 364

|  | C % | H % | N % | O % |
|---|---|---|---|---|
| calculated | 72.59 | 6.65 | 7.70 | 13.19 |
| found | 72.40–72.80 | 6.70–6.80 | 7.65–7.58 | 13.09 |

9-hydroxy-6-methyl-2-($\beta$-hydroxy-ethyl)-ellipticinium bromide:
$C_{20}H_{21}N_2O_2Br$
Molecular weight: 4.01

|  | C % | H % | N % | O % | Br % |
|---|---|---|---|---|---|
| calculated | 59.91 | 5.28 | 6.99 | 7.98 | 19.93 |
| found | 59.94–59.73 | 5.40–5.41 | 7.61–7.55 | 7.97–7.82 | 18.94–18.99 |

(by thin layer chromatography; Silicagel Merck F-254; solvent:mixture 4M/5 of butanol/acetic acid/water; Rf~0.37).

9-hydroxy-6-methyl-2-($\beta$-hydroxy-ethyl)-ellipticinium acetate:
(obtained by exchange of the latter on a Bio-Rad ® resin in the acetate form, in DMF).
$C_{22}H_{24}N_2O_4$
Molecular weight: 380
The elementary analysis confirmed this formula.
9-hydroxy-2,6-diethyl-ellipticinium iodide:
$C_{21}H_{23}N_2OI$, confirmed by elementary analysis.
Molecular weight: 446

|  | C % | H % | N % | O % | I % |
|---|---|---|---|---|---|
| calculated | 56.55 | 5.20 | 6.28 | 3.59 | 28.45 |
| found | 55.77–55.75 | 5.22–5.18 | 6.11–6.25 | 3.85–4.10 | 28.96–28.89 |

(by TLC in same conditions as above; Rf~0.33).
9-hydroxy-2,6-diethyl-ellipticinium acetate:
(obtained by exchange of the latter on a Bio-Rad ® resin in the acetate form, in DMF).
$C_{23}H_{26}N_2O_3$, confirmed by elementary analysis.
Molecular weight: 378.
9-hydroxy-5-ethyl-2-($\beta$-hydroxy-ethyl)-ellipticinium bromide:
$C_{21}H_{23}N_2O_2Br + \frac{1}{2}H_2O$
Molecular weight: 415+9

|  | C % | H % | N % | O % | Br % |
|---|---|---|---|---|---|
| calculated | 59.49 | 5.71 | 6.61 | 9.43 | 18.85 |
| found | 60.40–60.50 | 5.64–5.61 | 6.75–6.71 | 8.87 | 18.24 |

(by TLC in same conditions as above; Rf~0.35).
9-hydroxy-6-ethyl-2-($\beta$-hydroxy-ethyl)-ellipticinium acetate:
(obtained by exchange of the latter on a Bio-Rad ® resin in the acetate form, in DMF).
$C_{23}H_{26}N_2O_4$, confirmed by elementary analysis,
Molecular weight: 394.
9-ethoxy-2,6-diethyl-ellipticinium iodide:
$C_{23}H_{27}N_2OI + \frac{1}{2}H_2O$
Molecular weight: 474+9

|  | C % | H % | N % | O % | I % |
|---|---|---|---|---|---|
| calculated | 57.20 | 5.84 | 5.80 | 4.97 | 26.28 |
| found | 56.60–56.64 | 5.41–5.58 | 5.84–5.81 | 4.05–4.09 | 26.16–27.31 |

(by TLC as above; Rf~0.39).
9-ethoxy-2,6-diethyl-ellipticinium acetate:
(obtained by exchange of the latter on a Bio-Rad ® resin in the acetate form, in DMF).
$C_{25}H_{30}N_2O_3$, confirmed by elementary analysis.
Molecular weight: 406.
9-ethoxy-6-ethyl-2-($\beta$-hydroxy-ethyl)ellipticinium bromide:
$C_{23}H_{27}N_2O_2Br$, confirmed by elementary analysis
Molecular weight: 443.
(by TLC as above; Rf~0.33).
9-hydroxy-6-ethyl-2-($\beta$-hydroxy-ethyl)-ellipticinium acetate:
(obtained by exchange of the latter on a Bio-Rad ® resin in the acetate form, in DMF).
$C_{25}H_{30}N_2O_4$, confirmed by elementary analysis.
Molecular weight: 422.

EXAMPLE 10

9-hydroxy-2,6-diethyl-ellipticinium acetate was prepared, as hereafter described, according to the preferred method of this invention.

1. 6-methoxy-1,4-dimethyl-carbazole (a prior art product described in Aust. J. Chem.1967,28, p.2722)

In a flask (equipped with magnetic stirring, cooling means and a water removal system), a mixture of 117 g (0.80 mole) of 5-methoxy-indole, 300 ml of absolute ethanol, 92 g (0.80 mole) of hexane-2,5-dione (freshly rectified and 90 g of p-toluene-sulfonic acid (azeotropically dehydrated was heated with reflux for 1 hour and then cooled, and 250 ml of anhydrous toluene were added thereto. The mixture was heated again for gentle azeotropic distillation in order to remove the reaction water, i.e. approximately 30 ml of water, for about 2 hours.

After cooling, 200 ml of water were added, the toluene layer was separated by decantation, and the water layer was extracted with 100 ml of toluene.

The toluene solutions were gathered, washed twice with water, dried on anhydrous $CaCl_2$, filtered off and the toluene in excess was removed on a water bath under vacuum.

The residue was crystallized again from cyclohexane.
Yield: approximately 78 g. fine colorless crystals (M.P.)=137° C.

2. 6-hydroxy-1,4-dimethyl-carbazole

A solution of 30 g of 6-methoxy-1,4-dimethyl-carbazole in 300 g of absolutely anhydrous (water-free)

pyridine hydrochloride was heated with gentle reflux on 180°-190° C. for 5 hours.

After cooling, the mixture was poured onto ice, and alcalinized with concentrated ammonia to pH 6–6.5, and then dried, washed repeatedly with water and crystallized again from a mixture ethanol/water.

Yield: 22 g of fine colorless crystals.
M.P. = 171° C.
$C_{14}H_{13}NO$
Molecular weight: 211.26

|  | C % | H % | N % | O % |
| --- | --- | --- | --- | --- |
| calculated | 79.69 | 6.69 | 6.64 | 7.58 |
| found | 78.89 | 6.27 | 6.39 | 7.59 |

3. 6-benzoyl-oxy-1,4-dimethyl-carbazole 21 g (0.10 mole) of 6-hydroxy-1,4-dimethyl-carbazole were dissolved into a mixture of 200 ml of anhydrous acetone and 50 ml of triethylamine (dried on potash pellets). 17 g (0.12 mole) of freshly rectified benzoyl chloride were added dropwise and while a magnetic stirring of the mixture was maintained. The duration of the reaction was of 2 hours.

A precipitation of triethylamine hydrochloride was observed. The excess of acetone and of residual triethylamine was removed by heating on a water bath. The product was dissolved again into water and repeatedly extracted with $CHCl_3$. The chloroform solution was washed with water, then with a 5% solution of sodium bicarbonate and again with water, thereafter dried on $CaCl_2$, and filtered, and the chloroform in excess was removed.

The product was crystallized again from a minimum amount of $CHCl_3$.
$C_{21}H_{17}NO_2 + \frac{1}{2}H_2O$
Molecular weight: 315+9

|  | C % | H % | N % | O % |
| --- | --- | --- | --- | --- |
| calculated | 77.84 | 5.60 | 4.32 | 12.35 |
| found | 77.41 | 5.64 | 3.97–3.92 | 13 |

4. 9-ethyl-6-benzoyl-oxy-1,4-dimethyl-carbazole

In an apparatus equipped with a $CaCl_2$ trap, 16 g (0.05 mole) of 6-benzoyl-oxy-1,4-dimethyl-carbazole were dissolved into 120 ml of DMF (dried on molecular sieves). Under magnetic stirring, 1.35 g of 100% NaH were added thereto. In about 1 hour, the mono-sodium derivative was formed.

While externally cooling with ice water, 9 g of ethyl iodide were added dropwise, in 30 minutes.

The mixture was kept without stirring for one night. Thereafter, it was heated for one hour on a boiling water bath.

Most of the DMF was removed under deep vacuum. After cooling, the product was redissolved into ice water and several times extracted with $CHCl_3$.

The chloroform solution was washed with water, dried on $CaCl_2$, filtered, and the excess of $CHCl_3$ was eliminated.
$C_{23}H_{21}NO_2$
Molecular weight: 343.4

5. 9-ethyl-6-benzoyl-oxy-3-formyl-1,4-dimethyl-carbazole 41 g (0.12 mole) of the product of step 4 were dissolved into 200 ml of dry ortho-dichloro-benzene; then 22 g (0.17 mole) of freshly rectified N-methyl-formanilide were added, and 22 g (0.14 mole) of phosphorus oxychloride were added stepwise.

The whole mixture was heated for 3 hours on a boiling water bath. After cooling, the reaction product was poured carefully into a cold solution of 50 g of sodium acetate in 300 ml of water.

The benzene layer was separated by decantation and a steam extraction was used for removing the ortho-dichloro-benzene and the N-methyl-formanilide in excess. The residue was dissolved, under heating, into toluene and purified on coal.
$C_{24}H_{21}NO_3$
Molecular weight: 371.436.

6. 9-ethyl-6-benzoyl-oxy-3-($\beta,\beta$-dimethoxy-ethyl-iminomethyl)-1,4-dimethyl-carbazole A mixture of 18.60 g (0.05 mole) of the product (aldehyde) of step 5 and 50 ml of amino-acetaldehyde dimethylacetal was heated for 2 hours on a boiling water bath. Then 100 ml of anhydrous benzene were added and the water which had formed during the reaction was removed by azeotropic distillation of the mixture. The residue was crystallized again from benzene (or toluene).
$C_{28}H_{30}N_2O_4$
Molecular weight: 458.56.

7. 9-benzoyl-oxy-6-ethyl-ellipticine (base)

22 g (0.05 mole) of the product (azomethine) of step 6 were introduced into a solution of 600 g of orthophosphoric acid and 20 g of phosphorus pentoxyde.

The mixture was slowly heated up to 125°–130° C. and was kept at this temperature range for 20 minutes. After subsequent cooling, the reaction mixture was poured into 3 l of ice water, and neutralisation was carefully carried out, by means of ammonia, up to pH ~ 7.

A mixture of 9-benzoyl-oxy-6-ethyl-ellipticine and 9-hydroxy-6-ethyl-ellipticine was obtained, which could be separated by a column chromatography.

Pure $C_{26}H_{22}N_2O_2$ (title compound) was thus obtained.
Molecular weight: 394.48.

8. 9-hydroxy-6-ethyl-ellipticine (base)

10 g of the aforesaid mixture of the two ellipticines were heated with gentle reflux on a water bath for 30 minutes, in 100 ml of 95% ethanol and 10 ml concentrated HCl.

After cooling and drying, the title compound base was prepared. It was crystallized again from ethanol.
$C_{19}H_{18}N_2O$
Molecular weight: 290.37.

9. 9-hydroxy-2,6-diethyl-ellipticinium iodide (or 9-hydroxy-6-ethyl-ellipticinium iodoethylate)

10 g of 9-hydroxy-6-ethyl-ellipticine were dissolved into 100 ml of DMF previously dried on molecular sieves, and after cooling 5 ml of ethyl iodide were added thereto. The mixture was kept under magnetic stirring for several hours, until the maximum amount of halide precipitated out.

The product was dried and washed with anhydrous ether, and then crystallized again from absolute ethanol.

$C_{21}H_{23}N_2OI$
Molecular weight: 446

|  | C % | H % | N % | O % | I % |
|---|---|---|---|---|---|
| calculated | 56.55 | 5.20 | 6.28 | 3.59 | 28.45 |
| found | 55.77–55.75 | 5.22–5.18 | 6.11–6.25 | 3.85–410 | 28.96–28.89 |

(by thin layer chromatography (TLC); Silicagel Merck F-254; solvent:mixture 4/1/5 of butanol/acetic acid/-water; Rf~0.33).

10. 9-hydroxy-2,6-diethyl-ellipticinium acetate

The product of step 9 was dissolved into DMF while water was also stepwise added thereto, so that a 50/50, DMF/H₂O solvent was formed and a final concentration of approximately 2-10 mg/ml was obtained. This solution was then carefully degasified.

A column of appropriate anion exchange resin was prepared as follows:

Resin: Analytical Grade Anion Exchange Resin Bio-Rad ® AG I-X8, 100–200 mesh, in acetate form Amount of resin needed: the exchange capacity of this resin was 1.4 meq/ml of resine, or 3.2 meq/g of dry weight of resin, i.e. in this case 0.78 g of resin/g of product. The amount of resin actually used was of three times the amount strictly needed.

Elution medium: mixture 50/50 of DMF/H₂O

The resin was suspended in this mixture. The column was then fed and equilibrated, and the solution of iodide derivative (prepared as above described) was eluted on this column, thus giving a solution of 9-hydroxy-2,6-diethyl-ellipticinium acetate. Water was completely removed therefrom and DMF was partially removed. A precipitation from ether was conducted and, after filtration, the precipitated product was filtered off, washed with ether, and dried under vacuum in an exsiccator. A well water soluble orange powder was obtained (Yield: 95% in weight), from which one could prepare easily aqueous solution containing 4 mg/ml of said acetate.

$C_{23}H_{26}N_2O_3$
Molecular weight: 378.

PHARMACOLOGICAL TRAILS

1-9-hydroxy-ellipticinium iodomethylate

In order to test this product, it was put into hydrosoluble form, i.e. in the form of 9-hydroxy-2-methylellipticinium acetate.

To do this, a given amount of 9-hydroxyellipticinium iodomethylate, prepared as described in example 1-b), was dissolved in a minimal amount of pure dimethyl formamide. The product was diluted to 50% by the addition of distilled water and absorbed on a column (Pipette Pasteur type) of Amberlite CG-50. Washing was effected with a volume of distilled water of about 10 times the volume of the column and was then eluted with 0.1 mole hydrochloric acid.

It must be noted that it is important to operate quickly, in practice taking no longer than 60 minutes, as the solution is metastable.

The eluent was alkalinized with a solution of 1N soda to pH 12 and left to stand for 30 minutes. A precipitate formed, which was filtered on a special sterilization membrane and washed with 0.01 molar soda. Said precipitate was then put in solution again in 0.1 molar CH₃COOH. The pH was adjusted to 5.5 with a 0.1N soda solution and a clear solution of 9-hydroxy-2-methyl-ellipticinium acetate was obtained.

The biological activity of said compound was tested on two forms of leukemia: mouse L1210 leukemia and mouse P 388 leukemia.

The lethal dose $LD_O$ was 5 mg/kg of body weight of the animals used in the experiment.

A—A tumoral inoculum of $10^5$ L1210 leukemia cells was administered by the intraperitoneal way to twenty 2 to 3 months old DBA/2 strain female mice. 24 hours later, half of said mice received a single intraperitoneal injection of a variable dose of the compound to be tested and the same volume of solvent was administered to the other half of the mice by the same way; this latter half of the group of mice was therefore used as the control series. The mice were randomized in each experimental series.

Animals surviving for longer than 45 days were considered to be cured. The $LD_O$ lethal dose, i.e. 5 mg/kg, was taken as the basis of the therapeutic activity of the compounds of the invention.

The following table IV shows the results obtained by varying the dose of active compound injected.

TABLE IV

The therapeutic effect of variable doses (intraperitoneal) injection of a single dose of 9-hydroxy 2-methyl ellipticinium acetate for a tumoral inoculum of $10^5$ L1210 leukemia cells.

| Dose of 9-hydroxy 2-methyl-ellipticinium acetate as fraction of the sublethal dose of 5 mg/kg. | Mean survival in days of control mice | Mean survival in days of treated mice | % of tumoral cells killed by the treatment |
|---|---|---|---|
| 0.1 | 9.0 ± 0.4 | 11.3 ± 0.5 | 97 |
| 0.2 | 9.0 ± 0.4 | 12.2 ± 0.8 | 99.5 |
| 0.5 | 9.0 ± 0.4 | 12.5 ± 0.7 | 99.6 |
| 1 | 9.0 ± 0.4 | 15.7 ± 0.8 | 99.999 |

1 cured mouse surviving more than 45 days out of 20 mice.

B-The same procedure was used as in A, but after a tumoral inoculum of $10^5$ P 388 leukemia cells had been injected to the mice. The therapeutic activity of the 9-hydroxy 2-methyl-ellipticinium was similar on this mouse P 388 leukemia to that obtained on mouse L1210 leukemia, using the same doses.

From these results, and notably from table I above, it may be inferred that:
(1) 9-hydroxy 2-methyl-ellipticinium acetate is active at doses about 10 times smaller than the doses of 9-hydroxy-ellipticine necessary to obtain a comparable result. This is very advantageous both from a practical and an economic point of view, as not only are the problems connected with the solubility of the product, the method for injecting same, etc, very much less acute, but also the cost of the treatment is considerably lower.
(2) 9-hydroxy 2-methyl-ellipticinium acetate is more active than 9-hydroxy-ellipticine at the sublethal dose and kills 99.999% of tumoral cells, whereas 9-hydroxy-ellipticine would only kill 99.99% of said cells under the same conditions (that is to say, among other things, for a same inoculum).

It is obvious to the specialist that although one decimal of the percentage is involved in this result, this is extremely important as in this field of cancer chemotherapy it is of the utmost importance to be able to get as close as possible to the maximum results leading to a complete cure.

2-9-hydroxy 6-methyl-ellipticinium iodomethylate

Although this compound is much more soluble than the 9-hydroxy-ellipticinium iodomethylate tested as described in (1), the same hydrosolubilization technique was used, thus providing the corresponding acetate.

The $LD_O$ lethal dose was 50 mg/kg

Using the same procedure as described in (1) above, the results given in table V below were obtained.

TABLE V

Therapeutic effect of variable doses (intraperitoneal injection of a single dose) of 9-hydroxy-2,6-dimethyl-ellipticinium acetate for a tumoral inoculum of $10^5$ cells.

| Dose of 9-hydroxy 2,6-dimethyl-ellipticinium acetate as fraction of the sublethal dose oi 5 mg.kg | Mean survival in days of control mice | Mean survival in days of treated mice | % of tumoral cells killed by the treatment |
|---|---|---|---|
| 0.01 | 9.0 ± 0.4 | 10.3 ± 0.4 | 90 |
| 0.02 | 9.0 ± 0.4 | 10.4 ± 0.4 | 92 |
| 0.05 | 9.4 ± 0.4 | 12.7 ± 0.6 | 98 |
| 0.1 | 9.4 ± 0.4 | 14.0 ± 0.5 | 99.96 |
| 0.2 | 9.0 ± 0.4 | 13.4 ± 0.6 | 99.95 |
| 1 | 8.7 ± 0.5 | 16.1 ± 0.8 | 99.999 |

It will be seen from this table that:

the therapeutic index of 9-hydroxy-2,6-dimethyl-ellipticinium acetate is extremely high;

for a dose equivalent to 1/100th of the sublethal dose, the product was very active, as 90% of the leukemic cells were killed;

for a dose equivalent to only 1/10th of the sublethal dose, the activity observed was such that 99.96% of the leukemic cells were killed, which is equivalent to the therapeutic effect obtained with 9-hydroxy-ellipticine used at the sublethal dose, i.e. injecting 10 times as much of the product, which is too close to the lethal dose to be acceptable; at present, no other substance appears to have been found which has such a high therapeutic index on this L 1210 leukemia experimental system;

under the same experimental conditions, 9-hydroxy-2,6-dimethyl-ellipticinium acetate given at the sublethal dose killed 99.999% of the leukemic cells, which demonstrated a much greater antitumoral activity than that obtained with 9-hydroxy-ellipticine, which only killed 99.99% of the tumoral cells.

3-9-acetoxy-6-methyl-ellipticinium iodomethylate

Trials similar to those described under (1) above showed that the antitumoral activity of the water soluble 9-acetoxy-2,6-dimethyl-ellipticinium acetate is comparable with that of the 9-hydroxy-2,6-dimethyl-ellipticinium acetate. The sublethal dose was 50 mg/kg.

For said sublethal dose and under the same experimental conditions as given under (1), 99.999% of the leukemic cells were killed. 4. Results of pharmacological studies on same other compounds of this invention.

Similar tests on other compounds of this invention were conducted, as described above, on mice. The results thereof are gathered in table VI.

TABLE VI

Therapeutic effect in intraperitoneal (I.P.) or intravenous (I.V.) injection of a dose of compound in the acetate form for a tumoral inoculum of $10^5$ L1210 leukemia cells

| COMPOUND | Injection | Dose as a fraction of the sublethal dose | Mean survival in days for control mice | Mean survival in days for treated mice | $ILS^x$ % | % of killed cells |
|---|---|---|---|---|---|---|
| 9-hydroxy-2-(β-hydroxy-ethyl)-ellipticinium acetate | I.P. | 1 | 9.4 ± 0.4 | 18.5 ± 3.5 | 197 | 99.999 |
| | | 0.1 | 8.4 ± 0.4 | 13.4 ± 1.3 | 159 | 99.99 |
| | | 1.5 | 8.4 ± 0.7 | 23.7 ± 7.4 | 282 | 99.999 |
| | | 0.5 | 8.4 ± 0.7 | 18.3 ± 3.9 | 217 | 99.999 |
| $DL_o$ (I.P.): 10 mg/kg | | 0.1 | 8.4 ± 0.7 | 12.7 ± 1.7 | 151 | 99.96 |
| | | 0.05 | 8.4 ± 0.7 | 11.2 ± 1 | 133 | 99.4 |
| | | 0.01 | 8.4 ± 0.7 | 9.7 ± 0.7 | 115 | 90 |
| $DL_o$ (I.V.): 20 mg/kg | I.V. | 1 | 9.1 ± 0.6 | 13.3 ± 1 | 146 | 99.96 |
| | | 0.5 | 9.1 ± 0.6 | 12.8 ± 1.2 | 140 | 99.8 |
| | | 2 × 0.5 | 9.3 ± 0.5 | 13.2 ± 0.5 | 142 | |
| | | 3 × 0.25 | 9.3 ± 0.5 | 11.6 ± 1 | 125 | |
| | | 0.25 | 9.9 ± 0.6 | 12.0 ± 07 | 121 | 98 |
| 9-hydroxy-2-ethyl ellipticinium acetate | I.P. | 0.1 | 8.4 ± 0.4 | 14.7 ± 2.6 | 175 | ≈99.999 |
| | | 0.05 | 9.6 ± 0.7 | 12.7 ± 1.4 | 132 | 99.7 |
| | | 0.02 | 9.6 ± 0.7 | 12.7 ± 0.9 | 132 | 99.7 |
| $DL_o$ (I.P.):50 mg/kg | | 0.4 | 10.05 ± 0.3 | 16.6 ± 3.3 | 165 | ≈99.999 |
| | | 0.2 | 10.05 ± 0.3 | 22 ± 4.7 | 219 | ≈99.999 |
| $DL_{100}$ (I.P.):100 mg/kg | | 0.01 | 10.05 ± 0.3 | 12.3 ± 0.8 | 122 | 98.2 |
| | | 0.002 | | 11.45 ± 0.7 | 114 | 92 |
| | | 1 | 10.05 ± 0.5 | 15.80 ± 3.2 | 157 | ≈99.999 |
| | | 0.6 | | 18.9 ± 3.2 | 188 | ≈99.999 |
| $DL_o$ (I.V.):15 mg/kg | I.V. | 1 | 10.05 ± 0.5 | 12.5 ± 0.6 | 124 | 98.8 |
| $DL_{100}$ (I.V.) =:20 mg/kg | | 0.33 | | 11.9 ± 0.8 | 118 | 96.3 |
| 9-hydroxy-6-methyl-2-ethyl-ellipticinium acetate | I.P. | 0.6 | 8.1 ± 0.3 | 16.4 ± 2.9 | 202 | ≈99.999 |
| | | 0.2 | 8.1 ± 0.3 | 14.4 ± 1.6 | 178 | ≈99.999 |
| $DL_o$ (I.P.) =:50 mg/kg | | 0.1 | 8.1 ± 0.3 | 10.3 ± 0.1 | 127 | 98.2 |
| $DL_o$ (I.V.):5 mg/kg | I.V. | 1 | 8.5. ± 1 | 9.75 ± 0.8 | 115 | 90 |
| 9-acetoxy-2-ethyl-ellipticinium acetate | I.P. | 0.6 | 8.3 ± 0.5 | 17.8 ± 4.2 | 191 | ≈99.999 |
| | | 0.3 | 8.3 ± 0.5 | 16.7 ± 3.2 | 180 | ≈99.999 |
| | | 0.1 | 8.3 ± 0.5 | 14.6 ± 1.1 | 157 | 99.994 |

TABLE VI-continued

Therapeutic effect in intraperitoneal (I.P.) or intravenous (I.V.) injection of a dose of compound in the acetate form for a tumoral inoculum of $10^5$ L1210 leukemia cells

| COMPOUND | Injection | Dose as a fraction of the sublethal dose | Mean survival in days for control mice | Mean survival in days for treated mice | ILS$^x$ % | % of killed cells |
|---|---|---|---|---|---|---|
| $DL_o$ (I.P.):50 mg/kg | | 0.02 | 9.1 ± 0.5 | 12.5 ± 1 | 137 | 99.8 |
| | | 0.01 | | 12.2 ± 0.7 | 134 | 99.7 |
| | | 0.005 | | 10.4 ± 0.7 | 114 | 90 |
| 9-hydroxy-2-($\beta$-di-ethyl-amino-ethyl)-ellipticinium acetate | I.P. | 0.5 | 9.4 ± 0.4 | 18.4 ± 4.7 | 196 | ≈99.999 |
| | | 0.02 | 8.4 ± 0.4 | 11.7 ± 0.9 | 139 | 99.8 |
| | | 0.3 | 8.4 ± 0.7 | 20.4 ± 5.4 | 243 | ≈99.999 |
| | | 0.1 | 8.4 ± 0.7 | 14.5 ± 1.8 | 173 | 99.998 |
| $DL_o$ (I.P.):50 mg/kg | | 0.2 | 8.4 ± 0.7 | 12.7 ± 0.9 | 151 | 99.96 |
| | | 0.01 | 8.4 ± 0.7 | 11.5 ± 0.8 | 137 | 99.7 |
| | | 0.002 | 8.4 ± 0.7 | 10.0 ± 0.7 | 119 | 95 |
| $DL_o$ (I.V.):5 mg/kg | I.V. | 1 | 9.9 ± 0.6 | 11.1 ± 1 | 112 | 90 |
| 9-hydroxy-2-($\beta$-di-isopropyl-amino-ethyl)-ellipticinium acetate | I.P. | 1 | 9.9 ± 0.6 | 10.9 ± 1.3 | 110 | <90 |
| | | 0.1 | 9.7 ± 0.9 | 10.7 ± 0.8 | 110 | <90 |
| $DL_o$ (I.P.):10 mg/kg | | | | | | |
| 9-hydroxy-2-($\beta$-piperidino-ethyl)-ellipticinium acetate | I.P. | 1 | 9.7 ± 0.9 | 15.6 ± 3 | 171 | ≈99.999 |
| | | 0.2 | 9.7 ± 0.9 | 18.4 ± 3.9 | 202 | ≈99.999 |
| | | 0.1 | 9.7 ± 0.9 | 16.50 ± 3.5 | 181 | ≈99.999 |
| | | 0.02 | 9.7 ± 0.9 | 11.9 ± 0.9 | 131 | 99.4 |
| | | 0.01 | 9.7 ± 0.9 | 11.3 ± 0.6 | 124 | 98 |
| $DL_o$ (I.P.):50 mg/kg | | 0.005 | 9.7 ± 0.9 | 10.8 ± 0.9 | 119 | 96 |
| | | 0.002 | 9.7 ± 0.9 | 10.3 ± 0.4 | 113 | 90 |
| $DL_o$ (I.V.):10 mg/kg | | 1 | 9.3 ± 0.5 | 12.2 ± 0.8 | 131 | 99.4 |

$^x$ILS: increased life span.

Various modification of the compositions and method of the invention may be made without departing from the spirit or scope thereof and it is to be understood that the invention is to be limited only as defined in the appended claims.

What we claim is:

1. In a process for the synthesis of a pyrido[4,3-b]carbazole from a 6-methoxycarbazole, which includes the formation by formylation of a 3-formyl-carbazole and the formation by cyclization of a pyrido[4,3-b]carbazole, the improvement comprising:
   the preparation of a 9-hydroxy-pyrido[4,3-b]carbazole by; demethylating said 6-methoxy-carbazole thereby forming a 6-hydroxy-carbazole; benzoylating said 6-hydroxycarbazole thereby forming a 6-benzoyl-carbazole; and thereafter formylating said 6-benzoyl-carbazole in the 3-position and subjecting 3-formyl-6-benzoylcarbazole to cyclization conditions thereby forming 9-benzoyl-pyrido[4,3-b] carbazole.

2. A process according to claim 1 wherein after said cyclization said 9-benzoyl-pyrido[4,3-b]carbazole is saponified to convert the 9-benzoyl group to a 9-hydroxyl group.

3. A process according to claim 1 wherein said 6-benzoyl-carbazole has an —NH-group in the 9-position and wherein prior to said formylation, said 6-benzoyl-carbazole is reacted with a base and an alkyl halide to substitute an alkyl group of $C_1$ to $C_3$ carbon atoms for the "H" of said —NH-group.

4. A process according to claim 1 wherein said 9-hydroxy-pyrido[4,3-b]carbazole is formed by treating said 9-benzoyl-pyrido[4,3-b]carbazole with aqueous acid.

5. In a process for the synthesis of a pyrido[4,3-b]carbazole from a 6-hydroxy-carbazole, the improvement comprising the following reaction steps:
   (A) benzoylating said 6-hydroxy-carbazole thereby forming a 6-benzoyl-carbazole;
   (B) formylating said 6-benzoyl-carbazole thereby forming a 3-formyl-6-benzoyl-carbazole;
   (C) cyclizing said 3-formyl-6-benzoyl-carbazole thereby forming a 9-benzoyl-pyrido[4,3-b]-carbazole; and
   (D) saponifying said 9-benzoyl group thereby forming a 9-hydroxy-pyrido[4,3-b]carbazole.

6. A process according to claim 5 wherein said 6-hydroxy-carbazole in step (A) is 1,4-dimethyl-6-hydroxy-carbazole.

7. A process according to claim 5 wherein said 6-hydroxy-carbazole in Step (A) is reacted with benzoyl halide and base to form 6-benzoyl-carbazole.

8. A process according to claim 7 wherein said 9-hydroxy-pyrido[4,3-b]carbazole in Step (D) is formed by treating said 9-benzoyl-pyrido[4,3-b]carbazole with either aqueous acid or base.

9. A process according to claim 8 wherein said 3-formyl-6-benzoyl-carbazole in Step (B) is formed by reacting said 6-benzoyl-carbazole with N-methyl formanilide in the presence of phosphorus oxychloride.

10. A process according to claim 9 wherein said 3-formyl-6-benzoyl-carbazole is reacted with the alkyl acetal of a 2-amino-aldehyde forming a 3-($\beta,\beta$-dialkoxy-ethyl-imino-methyl)-6-benzoylcarbazole, which is cyclized in the presence of acid.

11. A process according to claim 9 wherein said acetal is dimethyl acetal of 2-aminoacetaldehyde and said cyclization is effected in the presence of a mixture of about 91% phosphoric acid and phosphorous pentoxide.

* * * * *